(12) United States Patent
Dochnahl et al.

(10) Patent No.: US 8,933,246 B2
(45) Date of Patent: *Jan. 13, 2015

(54) PROCESS FOR PREPARING 1-PHENYLPYRAZOLES

(71) Applicant: BASF SE, Ludwigshafen (DE)

(72) Inventors: Maximilian Dochnahl, Mannheim (DE); Gunter Lipowsky, Ladenburg (DE)

(73) Assignee: BASF SE, Ludwigshafen (DE)

( * ) Notice: Subject to any disclaimer, the term of this patent is extended or adjusted under 35 U.S.C. 154(b) by 73 days.

This patent is subject to a terminal disclaimer.

(21) Appl. No.: 13/738,230

(22) Filed: Jan. 10, 2013

(65) Prior Publication Data

US 2013/0131352 A1    May 23, 2013

Related U.S. Application Data

(63) Continuation of application No. 13/393,624, filed as application No. PCT/EP2010/062950 on Sep. 3, 2010, now Pat. No. 8,362,271.

(30) Foreign Application Priority Data

Sep. 4, 2009   (EP) .................................... 09169528

(51) Int. Cl.
| C07D 231/10 | (2006.01) |
| C07D 231/20 | (2006.01) |
| C07D 231/14 | (2006.01) |

(52) U.S. Cl.
CPC ............ *C07D 231/20* (2013.01); *C07D 231/14* (2013.01)
USPC ...................................................... 548/366.1

(58) Field of Classification Search
USPC ...................................................... 548/366.1
See application file for complete search history.

(56) References Cited

U.S. PATENT DOCUMENTS

| 6,054,592 | A | 4/2000 | Muller et al. | |
| 8,362,271 | B2 * | 1/2013 | Dochnahl et al. | .......... 548/371.1 |

FOREIGN PATENT DOCUMENTS

| DE | 44 23 612 | 1/1996 |
| WO | WO 99/62885 | 12/1999 |

OTHER PUBLICATIONS

Antilla, Jon C. "Copper-Diamine-Catalyzed N-Arylation of Pyrroles, Pyrazoles, Indazoles, Imidazoles, and Triazoles", J. Org. Chem., 2004, pp. 5578-5587, vol. 69.

Cristau, Henri-Jean, et al., "Mild Conditions for Copper-Catalysed N-Arylation of Pyrazoles", Eur. J. Org. Chem., 2004, pp. 695-709.

Park, Kyugng-Ho, et al. "Novel Migration of Aryl Group in 3-Trifluoro-mehtylpyrazol aryl ether", Bull. Korean Chem. Soc., 1995, pp. 799-801, vol. 16, No. 9.

Tironi, Carla, et al., "Pyrazole sulfonamides: Nitroderivatives of 1-phenyl-3-sulfanilamidopyrazole", IL Farmaco, 1990, pp. 473-478, vol. 45, No. 4.

* cited by examiner

*Primary Examiner* — Samantha Shterengarts
(74) *Attorney, Agent, or Firm* — Brinks Gilson & Lione

(57) ABSTRACT

The present invention to a process for preparing 1-phenylpyrazoles of the formula I

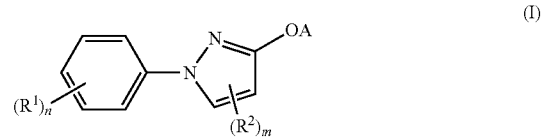

in which each $R^1$ is independently selected from chlorine, fluorine, alkyl, haloalkyl, alkoxy and haloalkoxy; n is 1, 2 or 3; each $R^2$ is independently selected from cyano, nitro, halogen, alkyl, haloalkyl, alkoxy, haloalkoxy, alkylthio and alkoxycarbonyl; m is 0, 1 or 2; A is alkyl, aryl or aryl-$C_1$-$C_4$-alkyl, where A optionally bears 1, 2, 3 or 4 substituents comprising reacting a phenyl halide of the formula (II) with a pyrazole derivative of the formula (III)

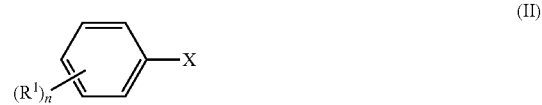

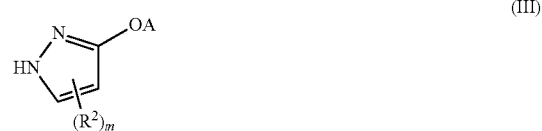

in which
X is chlorine, iodine or bromine; and
$R^1$, n, $R^2$, m and A are each as defined above,
in the presence of a base and a catalytic system comprising a ligand and a metal compound selected from palladium compounds, iron compounds and copper compounds.

9 Claims, No Drawings

PROCESS FOR PREPARING 1-PHENYLPYRAZOLES

CROSS-REFERENCE TO RELATED APPLICATIONS

This application is a continuation of U.S. application Ser. No. 13/393,624, filed Mar. 1, 2012, now U.S. Pat. No. 8,362,271, which application is a national stage application of International Application No. PCT/EP2010/062950, filed Sep. 3, 2010, the entire contents of which is hereby incorporated herein by reference. This application also claims priority under 35 U.S.C. §119 to European Patent Application No. 09169528.8 filed Sep. 4, 2009, the entire contents of which is hereby incorporated herein by reference.

DESCRIPTION

The present invention relates to a process for preparing 1-phenylpyrazoles. In particular, the invention relates to a process for preparing 1-phenylpyrazoles by C—N coupling of a phenyl halide and a pyrazole compound.

1-Phenylpyrazols are of great interest especially as pharmaceutical and pesticide pharmacophors, and as precursors of such active ingredients. Pyraclostrobine is a prominent representative of a pesticidal N-phenylpyrazole derivative.

The most important method for preparing this class of heterocycles involves the double condensation of 1,3-diketones with phenyl hydrazine or its derivatives. This method has a wide scope not only because of the readily availability of 1,3-diketones but also because one carbonyl of the diketone starting material can be replaced by an acetal, a hemiacetal, a chlorovinyl group, dihalides, etc.

Despite its versatility, the known method may require reaction conditions incompatible with many functional groups. Also, 1-phenylpyrazole compounds with certain substitution patterns may not or only with difficulties be accessible by existing methodologies.

Thus, there is an ongoing need for a process for preparing 1-phenylpyrazoles by coupling larger, functionalized molecules.

Transition metal-catalyzed cross-coupling of nitrogen nucleophiles with carbon electrophiles has emerged as a powerful tool in synthetic organic chemistry. Common electrophiles include aryl and vinyl halides, triflates and sulfonates. The nucleophiles being used comprise primary and secondary amines, ammonia, anilines, amides and carbamates. C—N couplings of aromatic nitrogen heterocycles, such as pyrazoles have also been investigated. C. Tironi, R. Fruttero and A. Garrone in Farmaco 1990, 45 (4), p. 473-478 describe the reaction of 3-acetylaminopyrazole with bromonitrobenzenes in the presence of potassium carbonate, copper(I) oxide and pyridine, to obtain 3-acetylamino-1-(nitrophenyl)-pyrazole.

K. H. Park et al. in Kor. Chem. Soc. 16(9), p. 799-801 (1995) describe the reaction of 5-hydroxy-3-trifluoromethylpyrazole with 3,4-dichloronitrobenzene in the presence of potassium carbonate in dimethylformamide. 1-(2-Chloro-4-nitrophenyl)-5-hydroxy-3-trifluoromethyl-pyrazole was obtained as the main reaction product.

WO 99/62885 makes reference to a synthetic method where a 3,5-disubstituted pyrazole is reacted with nitrobenzene substituted in the 4-position with a leaving group such as a halogen in the presence of a base.

These prior art references describe the use of aryl electrophiles where a halogen leaving group is activated by a nitro group.

It was an object of the present invention to provide a process for preparing 1phenylpyrazoles from phenylhalides where the phenyl ring is substituted by substituents different from a nitro group. The process should additionally be performable inexpensively and be based on selective conversions.

The object is achieved by the process described in detail below.

The present invention provides a process for preparing 1-phenylpyrazoles of the general formula (I)

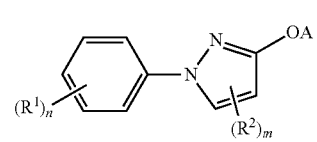

in which
each $R^1$ is independently selected from chlorine, fluorine, $C_1$-$C_4$-alkyl, $C_1$-$C_4$-haloalkyl, $C_1$-$C_4$-alkoxy and $C_1$-$C_4$-haloalkoxy;
n is 1, 2 or 3;
each $R^2$ is independently selected from cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkoxycarbonyl;
m is 0, 1 or 2;
A is $C_1$-$C_{12}$-alkyl, aryl or aryl-$C_1$-$C_4$-alkyl, where A optionally bears 1, 2, 3 or 4 substituents which are selected from halogen, cyano, nitro, $C_1$-$C_4$-alkyl, $C_1$-$C_4$-haloalkyl, $C_1$-$C_4$-alkoxy, $C_1$-$C_4$-haloalkoxy, a group $R^a$, a group $R^b$, a group $R^c$ and a group $R^d$

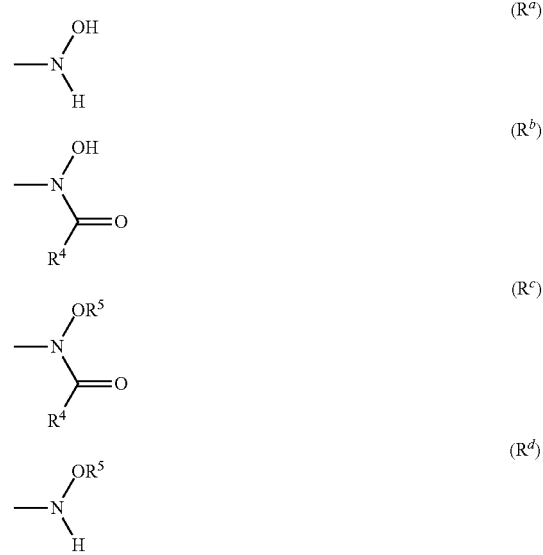

in which
$R^4$ is H, $C_1$-$C_4$-haloalkyl, $C_1$-$C_4$-alkoxy, $C_1$-$C_4$-haloalkoxy, aryl, aryloxy, aryl-$C_1$-$C_4$-alkoxy, where the aryl groups in the three latter radicals optionally bear 1, 2, 3 or 4 substituents which are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and $R^5$ is $C_1$-$C_4$-alkyl, $C_1$-$C_4$-haloalkyl or aryl-$C_1$-$C_4$-alkyl, where the aryl group in the latter radical optionally bears 1, 2, 3 or 4 substituents which are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

comprising the following step
(i) reacting a phenyl halide of the formula (II) with a pyrazole derivative of the formula (III)

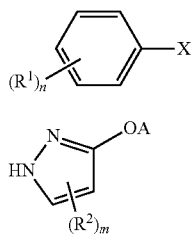

(II)

(III)

in which
X is chlorine, iodine or bromine; and
$R^1$, n, $R^2$, m and A are each as defined above;
in the presence of a base and a catalytic system comprising a ligand and a metal compound selected from palladium compounds, iron compounds or copper compounds.

In the context of the present invention, the terms used generically are defined as follows:

The prefix $C_x$-$C_y$ denotes the number of possible carbon atoms in the particular case.

The term "halogen" denotes in each case fluorine, bromine, chlorine or iodine, especially fluorine, chlorine or bromine.

The term "$C_1$-$C_4$-alkyl" denotes a linear or branched alkyl radical comprising from 1 to 4 carbon atoms, such as methyl, ethyl, propyl, 1-methylethyl(isopropyl), butyl, 1-methyl-propyl(sec-butyl), 2-methylpropyl(isobutyl) or 1,1-dimethylethyl(tert-butyl).

The term "$C_1$-$C_{12}$-alkyl" denotes a linear or branched alkyl radical comprising from 1 to 12 carbon atoms. Examples are, as well as the radicals specified for $C_1$-$C_4$-alkyl, pentyl, hexyl, heptyl, octyl, 2-ethylhexyl, nonyl, decyl, undecyl, dodecyl, 2-propylheptyl, 3-butyloctyl and positional isomers thereof.

The term "cycloalkyl" denotes monocyclic saturated hydrocarbon groups having 3 to 6 ($C_3$-$C_6$-cycloalkyl), 3 to 8 ($C_3$-$C_8$-cycloalkyl) or 3 to 10 ($C_3$-$C_{10}$-cycloalkyl) carbon ring members, such as cyclopropyl, cyclobutyl, cyclopentyl, cyclohexyl, cycloheptyl, cyclooctyl, cyclononyl and cyclodecyl;

The term "$C_1$-$C_4$-haloalkyl", as used herein and in the haloalkyl units of $C_1$-$C_4$-haloalkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, di-chlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluorobutyl, 3-fluorobutyl, 4-fluorobutyl and the like.

The term "$C_1$-$C_4$-alkoxy" denotes straight-chain or branched saturated alkyl groups comprising from 1 to 4 carbon atoms, which are bound via an oxygen atom to the remainder of the molecule. Examples of $C_1$-$C_4$-alkoxy are methoxy, ethoxy, n-propoxy, 1-methylethoxy(isopropoxy), n-butoxy, 1-methylpropoxy(sec-butoxy), 2-methylpropoxy (isobutoxy) and 1,1-dimethylethoxy(tert-butoxy).

The term "$C_1$-$C_4$-haloalkoxy" describes straight-chain or branched saturated haloalkyl groups comprising from 1 to 4 carbon atoms, which are bound via an oxygen atom to the remainder of the molecule. Examples thereof are chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy, 1-chloro-1,2,2-trifluoroethoxy, pentafluoro-ethoxy, 3,3,3-trifluoroprop-1-oxy, 1,1,1-trifluoroprop-2-oxy, 3,3,3-trichloroprop-1-oxy, 1-chlorobutoxy, 2-chlorobutoxy, 3-chlorobutoxy, 4-chlorobutoxy, 1-fluorobutoxy, 2fluorobutoxy, 3-fluorobutoxy, 4-fluorobutoxy and the like.

The term "$C_1$-$C_4$-alkoxycarbonyl" denotes alkoxy radicals having from 1 to 4 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl.

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "hetaryl" denotes aromatic radicals having from 1 to 4 heteroatoms which are selected from O, N and S. Examples thereof are 5- and 6-membered hetaryl radicals having 1, 2, 3 or 4 heteroatoms selected from O, S and N, such as pyrrolyl, furanyl, thienyl, pyrazolyl, imidazolyl, oxazolyl, isoxazolyl, thiazolyl, isothiazolyl, triazolyl, tetrazolyl, pyridyl, pyrazinyl, pyridazinyl, pyrimidyl and triazinyl.

The term "aryl-$C_1$-$C_4$-alkyl" denotes aryl radicals which are bound via a $C_1$-$C_4$-alkyl group to the remainder of the molecule. Examples thereof are benzyl, 2-phenylethyl(phenethyl) and the like.

The term "aryl-$C_1$-$C_4$-alkoxy" denotes aryl-$C_1$-$C_4$-alkyl radicals as defined above which are bound via an oxygen atom to the remainder of the molecule. Examples thereof are benzyloxy, fluorenylmethoxy and the like.

The term "$C_1$-$C_4$-alkylthio "($C_1$-$C_4$-alkylsulfanyl: $C_1$-$C_4$-alkyl-S—)" denotes straight-chain or branched saturated alkyl radicals having 1 to 4 carbon atoms which are bound via a sulfur atom to the remainder of the molecule. Examples for $C_1$-$C_4$-alkylthio include methylthio, ethylthio, propylthio, 1-methylethylthio, butylthio, 1-methylpropylthio, 2methylpropylthio and 1,1-dimethylethylthio.

The remarks made below regarding preferred embodiments of the process according to the invention, especially regarding preferred meanings of the variables of the different reactants and products and of the reaction conditions of the process, apply either taken alone or, more particularly, in any conceivable combination with one another.

In the compounds of the formulae (I), (Ia), (II), (IV), (V) and (VI) n is preferably 0, 1 or 2 and especially preferably 0 or 1. When n is 1, $R^1$ is preferably in the para or meta position to the attachment point of the pyrazole moiety or to the 1-position of the radical X in a compound II.

In the compounds of the formulae (I), (Ia), (II), (IV), (V) and (VI) $R^1$ is preferably chlorine, fluorine, $C_1$-$C_2$-alkyl, $C_1$-$C_2$-haloalkyl, $C_1$-$C_2$-alkoxy or $C_1$-$C_2$-haloalkoxy. $R^1$ is more preferably chlorine, fluorine, $C_1$-$C_2$-alkyl or $C_1$-$C_2$-haloalkyl and even more preferably chlorine, methyl or halomethyl. Specifically, $R^1$ is 4-Cl, 3-Cl, 4-methyl, 3-methyl, 2-methyl, 4-methoxy, 3-methoxy, 3-chloromethyl, 4-chloromethyl, 4-trifluoromethyl, 3-trifluoromethyl, 3-chloromethoxy, 4-chloromethoxy, 4-trifluoromethoxy, 3-trifluoromethoxy, 3,4-$Cl_2$, 2,4-$Cl_2$, 3,4-dimethyl, 2,4-dimethyl, 3,4-dimethoxy or 2,4-dimethoxy. The statements of position relate to the 1-position through which the phenyl radical deriving from the compound of the formula (II) is bonded to the pyrazole ring or to the 1-position of the radical X in the phenyl halide II.

In the compounds of the formulae (I), (Ia), (III), (IIIa), (IV), (V) and (VI) m is preferably 0 or 1 and especially preferably 0.

In the compounds of the formulae (I), (Ia), (III), (IIIa), (IV), (V) and (VI) $R^2$ is preferably halogen, $C_1$-$C_2$-alkyl, $C_1$-$C_2$-haloalkyl, $C_1$-$C_2$-alkoxy, $C_1$-$C_2$-haloalkoxy, or $C_1$-$C_2$-alkoxycarbonyl. $R^2$ is more preferably chlorine, fluorine, $C_1$-$C_2$-alkyl, $C_1$-$C_2$-haloalkyl or $C_1$-$C_2$-alkoxycarbonyl and even more preferably chlorine, fluorine, methyl, halomethyl or methoxycarbonyl.

In the compounds of the formulae (I) and (III) A is preferably $C_1$-$C_8$-alkyl that optionally bears 1, 2, or 3 substituents selected from halogen, $C_1$-$C_4$-alkoxy, $C_1$-$C_2$-haloalkoxy, a group $R^a$, a group $R^b$, a group $R^c$ and a group $R^d$, or aryl-$C_1$-$C_2$-alkyl that optionally bears 1, 2 or 3 substituents which are selected from nitro, halogen, $C_1$-$C_2$-alkyl, $C_1$-$C_2$-haloalkyl, $C_1$-$C_2$-alkoxy, $C_1$-$C_2$-haloalkoxy, a group $R^a$, a group $R^b$, a group $R^c$ and a group $R^d$. A is more preferably benzyl that bears 1 or 2 substituents which are selected from nitro, halogen, a group $R^a$, a group $R^b$, a group $R^c$ and a group $R^d$ and even more preferably benzyl that bears in the ortho position nitro, a group $R^a$, a group $R^b$, a group $R^c$ or group $R^d$.

In the compounds of the formulae (I), (III), (V) and (VI) $R^4$ is preferably H, $C_1$-$C_2$ alkyl, $C_1$-$C_2$-haloalkyl, $C_1$-$C_2$-alkoxy, $C_1$-$C_2$-haloalkoxy, aryl, aryl-$C_1$-$C_2$-alkoxy, where the aryl groups in the two latter radicals optionally bear 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^4$ is more preferably $C_1$-$C_2$-alkoxy, $C_1$-$C_2$-haloalkoxy or benzyloxy, where the phenyl group of the latter radical optionally bears 1, 2 or 3 substituents which are selected from halogen, $C_1$-$C_2$-alkyl, $C_1$-$C_2$-haloalkyl and $C_1$-$C_2$-alkoxy. $R^4$ is even more preferably methoxy, halomethoxy or benzyloxy.

In the compounds of the formulae (I), (III) and (VI) $R^5$ is preferably $C_1$-$C_2$-alkyl, $C_1$-$C_2$-haloalkyl or aryl-$C_1$-$C_2$-alkyl, where the aryl group in the latter radical optionally bears 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^5$ is more preferably $C_1$-$C_2$-alkyl or $C_1$-$C_2$-haloalkyl and even more preferably methyl or halomethyl.

In the compounds of the formula (II) X is preferably iodine or bromine and more preferably bromine.

In the compounds of the formulae (Ia), (IIIa), (IV), (V) and (VI) p is preferably 0, 1 or 2 and especially preferably 0 or 1. When p is 1, $R^3$ is preferably in the para or meta position to the attachment point of the methylene bridge.

In the compounds of the formulae (Ia), (IIIa), (IV), (V) and (VI) $R^3$ is preferably halogen, $C_1$-$C_2$ alkyl, $C_1$-$C_2$-haloalkyl, $C_1$-$C_2$-alkoxy or $C_1$-$C_2$-haloalkoxy. $R^3$ is more preferably chlorine, fluorine, $C_1$-$C_2$-alkyl or $C_1$-$C_2$-haloalkyl and even more preferably chlorine, fluorine, methyl or halomethyl.

Examples of compounds of formula II are compounds of formula IIa

(IIa)

in which X has the general or preferred meaning given above.

Examples of compounds of the formula III are compounds of the formula IIIa

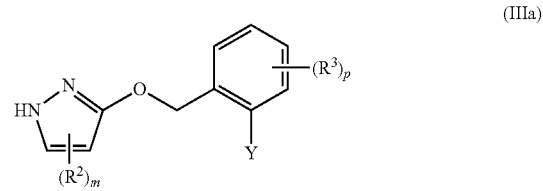

(IIIa)

in which
each $R^3$ is independently selected from halogen, cyano, $C_1$-$C_4$-haloalkyl, $C_1$-$C_4$-alkoxy and $C_1$-$C_4$-haloalkoxy;
p is 0, 1, 2 or 3;
Y is nitro, a group $R^a$, a group $R^b$, a group $R^c$ or a group $R^d$; and
$R^2$, m, $R^a$, $R^b$, $R^c$ and $R^d$ are each as defined above.

The inventive conversions described hereinafter are performed in reaction vessels customary for such reactions, the reaction being configurable in a continuous, semicontinuous or batchwise manner. In general, the particular reactions will be performed under atmospheric pressure. The reactions may, however, also be performed under reduced or elevated pressure.

The conversion in step (i) of the process according to the invention for preparing substituted 1-phenylpyrazoles I is a cross-coupling reaction leading to the formation of a C—N bond. The reaction is effected by contacting the starting compounds, i.e. an phenyl halide II and a pyrazole derivative III, and also a base and a catalytic system, preferably in a solvent, under suitable reaction conditions.

In general, step (i) is performed under temperature control. The reaction is typically effected in a closed or unclosed reaction vessel with stirring and heating apparatus.

The reactants can in principle be contacted with one another in any desired sequence. For example, the phenyl halide II, if appropriate dissolved in a solvent or in dispersed form, can be initially charged and admixed with the pyrazole derivative III or, conversely, the pyrazole derivative III, if appropriate dissolved in a solvent or in dispersed form, can be initially charged and admixed with the phenyl halide II. Alternatively, the two reactants can also be added simultaneously to the reaction vessel. The catalytic system and the base can, independently of each other, be added before or after the addition of one of the reactants or else together with one of the reactants, either in a solvent or in bulk. As an alternative to their joint addition the two components of the catalytic system, the ligand and the metal compound, can be added separately to the reaction vessel. Both of them can independently of one another be added before or after the addition of one of the reactants or else together with one of the reactants.

It has been found to be appropriate to initially charge the reaction vessel with the phenyl halide II, the pyrazole derivative III, the base and the metal compound and one or more ligands jointly. After exchanging the atmosphere to nitrogen or argon, the solvent is added.

Suitable solvents depend in the individual case on the selection of the particular reactants and reaction conditions. It has generally been found to be advantageous to use an aprotic organic solvent for the reaction of the compounds (II) with the compounds (III). Useful aprotic organic solvents here include, for example, aliphatic $C_3$-$C_6$-ethers, such as 1,2-dimethoxyethane (DME), diethylene glycol dimethyl ether (diglyme), diethyl ether, dipropyl ether, methyl isobutyl ether, tert-butyl methyl ether and tert-butyl ethyl ether, aliphatic hydrocarbons, such as pentane, hexane, heptane and octane, and also petroleum ether, cycloaliphatic hydrocarbons, such as cyclopentane and cyclohexane, alicyclic $C_3$-$C_6$-ethers, such as tetrahydrofuran (THF), tetrahydropyran, 2-methyltetrahydrofuran, 3-methyltetrahydrofuran and 1,4-dioxane, aromatic hydrocarbons, such as benzene, toluene, the xylenes and mesitylene, short-chain ketones, such as acetone, ethyl methyl ketone and isobutyl methyl ketone, amides such as dimethylformamide (DMF), dimethylacetamide and N-methylpyrrolidone (NMP), dimethyl sulfoxide (DMSO), acetonitrile, or mixtures of these solvents with one another.

If the catalytic system includes a copper compound and in particular a copper(I) compound, the solvent for the conversion in step (i) is preferably selected from aliphatic $C_3$-$C_6$ ethers, alicyclic $C_3$-$C_6$-ethers, aromatic hydrocarbons and mixtures thereof, and more preferably from DME, diglyme, THF, 1,4-dioxane, toluene and mixtures thereof. In this context toluene, 1,4-dioxane and DME are particularly preferred solvents for the conversion in step (i).

If the catalytic system includes an iron compound and in particular an iron(III) compound, the solvent for the conversion in step (i) is preferably selected from aliphatic $C_3$-$C_6$-ethers, alicyclic $C_3$-$C_6$-ethers, aromatic hydrocarbons, amides, DMSO and mixtures thereof, and more preferably from 1,4-dioxane, THF, toluene, NMP, DMF, DMSO and mixtures thereof. In this context DMF, DMSO, 1,4-dioxane and mixtures thereof are particularly preferred solvents for the conversion in step (i).

If the catalytic system includes a palladium compound the solvent for the conversion in step (i) is preferably selected from aliphatic $C_3$-$C_6$-ethers, alicyclic $C_3$-$C_6$-ethers, aromatic hydrocarbons, amides, DMSO and mixtures thereof, and more preferably from diethyl ether, THF, toluene, NMP, DMF, DMSO and mixtures thereof. In this context toluene is the particularly preferred solvent for the conversion in step (i).

The total amount of the solvent used in step (i) of the process according to the invention is typically in the range from 200 to 5000 g and preferably in the range from 300 to 4000 g, based on 1 mol of the pyrazole derivative III.

Preference is given to using solvents which are essentially anhydrous, i.e. have a water content of less than 1000 ppm and especially not more than 100 ppm.

In a preferred embodiment of the invention, in step (i), the phenyl halide of the formula II is used in an amount of 0.1 to 1.5 mol, more preferably of 0.5 to 1.2 mol, even more preferably of 0.7 to 0.9 mol and especially of 0.75 to 0.85 mol, based in each case on 1 mol of the pyrazole derivative of the formula III.

Pyrazole derivatives of the formula (III) can be prepared by customary processes. In case the variable A is an optionally substituted benzyl group, they are obtainable, for instance, by etherifying the corresponding 3-hydroxypyrazole that may carry a temporary N-protection group such as acetyl, with the corresponding benzyl bromide in the presence of a base, as described, for example, in WO 96/01256 and WO 99/06373. Suitable 3-hydroxypyrazoles can in turn be prepared for instance by reacting hydrazine either with the corresponding propiolic acid ester, as described for example in EP 0680954 A2, or with the corresponding (E)-methyl-3-methoxyacrylate, as described for example in G. A. Erler, W. Holzer, Molbank 2006, M464. The phenyl halides of the formula (II) are either commercially available or can be produced by standard methods well known in the art.

For the conversion in step (i) of the process according to the invention preferably those pyrazole derivatives of the formula (III) are employed that correspond to formula (IIIa)

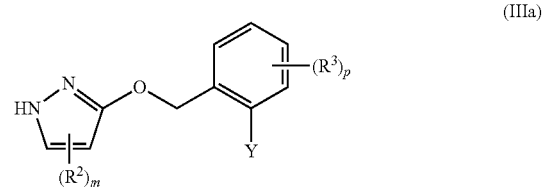

(IIIa)

in which
each $R^3$ is independently selected from halogen, cyano, $C_1$-$C_4$-alkyl, $C_1$-$C_4$-haloalkyl, $C_1$-$C_4$-alkoxy and $C_1$-$C_4$-haloalkoxy, p is 0, 1, 2 or 3, Y is halogen, nitro, a group $R^a$, a group $R^b$, a group $R^c$ or a group $R^d$, and $R^2$, m, $R^a$, $R^b$, $R^c$ and $R^d$ are each as defined herein before.

According to a preferred embodiment of the invention in step (i) those 3-benzyloxypyrazoles IIIa are employed in which Y represents a bromine, nitro or a group $R^c$ and the variables $R^2$, $R^3$, m and p have the meanings mentioned herein as preferred.

According to a particularly preferred embodiment of the invention in step (i) those 3-benzyloxypyrazoles IIIa are employed in which Y represents nitro or a group $R^c$, specifically nitro, and the variables m and p both are 0.

It is suspected that the mechanism of the reaction in step (i) corresponds to the mechanism proposed for similar transition metal catalyzed cross-coupling reactions. Accordingly, the first step of a catalytic cycle involves the oxidative addition of the metal compound of the catalytic system into the phenyl-halogen bond of compound (II) to form a metal ion intermediate, to which in the next step a nucleophile derived from compound (III) is transferred. The subsequent step is a reductive elimination that yields the coupled product (I) and regenerates the active metal compound species. Alternatively, at least if a catalytic system including a copper compound is used, the reaction mechanism may involve a similar catalytic cycle in which, however, the oxidation state of copper does not change. As a further possibility in the first step of the catalytic cycle the copper compound of the catalytic system may first interact with the nucleophile derived from compound (III) instead of with the phenyl halide II.

Suitable catalytic systems for the reaction of a compound II with a compound III in step (i) of the process according to the invention are preferably selected from
a) palladium catalysts in which palladium has an oxidation state of 0 or 2,
b) iron catalysts in which iron has an oxidation state 2 or 3, and c) copper catalysts in which copper has an oxidation state 0, 1 or 2.

The catalytic system of the process of the invention can be employed in the form of a preformed metal complex which comprises the metal compound and one or more ligands. Alternatively, the catalytic system is formed in situ in the reaction mixture by combining a metal compound, herein also termed pre-catalyst, with one or more suitable ligands to form a catalytically active metal complex in the reaction mixture.

Suitable pre-catalysts are selected from neutral metal complexes, oxides and salts of palladium, iron or copper. Useful palladium(II) salts for this purpose are, for example, bis[dibenzylideneacetone]palladium(0), tris[dibenzylideneacetone]dipalladium(0), palladium(II) chloride, bis(acetonitrile)palladium(II) chloride and palladium(II) acetate, of which bis[dibenzylideneacetone]palladium(0), tris[dibenzylideneacetone]dipalladium(0) are preferred. Useful iron (III) pre-catalysts are iron(III) chloride, iron(III) acetylacetonate and iron(III) oxide. Useful copper(I) pre-catalysts are copper(I) chloride, copper(I) bromide, copper(I) iodide, copper(I) thiophene-2-carboxylate and copper(I) oxide.

Suitable ligands of the catalytic system for the conversion in step (i) of the process according to the invention are, for example, mono- or bidentate phosphines of the formulae VII and VIII shown below

(VII)

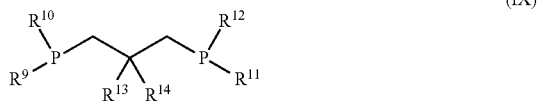

(VIII)

in which $R^6$ to $R^{12}$ are each independently $C_1$-$C_8$-alkyl, $C_5$-$C_8$-cycloalkyl, adamantyl, aryl-$C_1$-$C_2$-alkyl, ferrocenyl or aryl which is optionally substituted by $C_1$-$C_4$-alkyl, $C_1$-$C_4$-alkoxy, fluorine or chlorine, and T is ferrocenediyl or a linear $C_2$-$C_5$-alkanediyl which is optionally substituted by $C_1$-$C_8$-alkyl or $C_3$-$C_6$-cycloalkyl and is optionally part of one or two mono- or bicyclic rings which are unsubstituted or substituted.

More particularly, T in the compound of the formula VIII is $C_2$-$C_4$-alkylene, $C_0$-$C_1$-alkyleneferrocenyl, 1,2'-biphenyl-2,2'-diyl or 1,1-binaphthyl-2,2'-diyl, where the latter four groups may optionally be substituted by $C_1$-$C_8$-alkyl or $C_1$-$C_4$-alkoxy, and where $C_2$-$C_4$-alkylene may additionally have one or more substituents selected from $C_3$-$C_7$-cycloalkyl, aryl and benzyl. In this connection, 1 to 4 carbon atoms of the $C_2$-$C_4$-alkylene may be part of a $C_3$-$C_7$-cycloalkyl ring. Aryl here is naphthyl or optionally substituted phenyl. Aryl is preferably phenyl or tolyl, more preferably phenyl. $C_0$-$C_1$-Alkyleneferrocenyl is especially ferrocenediyl, where each one of the two phosphorus atoms is bonded to a different cyclopentadiene moiety of the ferrocene, or methylene-ferrocenyl, where one of the phosphorus atoms is bonded via the methylene group to a cyclopentadiene, the second phosphorus atom is bonded to the same cyclopentadiene, and the methylene group may optionally have 1 or 2 further substituents selected from Monodentate complex ligands of the formula VII preferred herein are those in which $R^6$, $R^7$ and $R^8$ are each optionally substituted phenyl, for example triphenylphosphine (TPP), and those in which $R^6$, $R^7$ and $R^8$ are each $C_1$-$C_6$-alkyl, $C_5$-$C_8$-cycloalkyl, adamantyl, or optionally substituted biphenyl, for example di-1-adamantyl-n-butylphosphine, tri-tert-butylphosphine (TtBP), methyldl-tert-butylphosphine, tricyclo-hexylphosphine, 2-(dicyclohexylphosphino)biphenyl and 2-dicyclohexylphosphino-2',4',6'-tri-i-propyl-1,1'-biphenyl(X-Phos). In addition, it is also possible to use phosphites, for example tris(2,4-di-tert-butylphenyl)phosphite (cf. A. Zapf et al., Chem. Eur. J. 2000, 6, 1830).

Bidentate complex ligands of the formula VIII preferred herein are those that correspond to the formula IX:

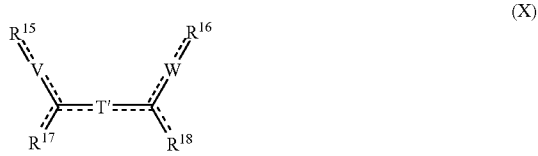

(IX)

in which $R^9$ to $R^{12}$ are each as defined above and are preferably each independently phenyl which optionally bears one to three substituents selected from methyl, methoxy, fluorine and chlorine. $R^{13}$ and $R^{14}$ are each independently hydrogen, $C_1$-$C_8$-alkyl or $C_3$-$C_6$-cycloalkyl, or $R^{13}$ and $R^{14}$ form, together with the carbon atom to which they are bonded, a 3- to 8-membered ring which is optionally substituted by $C_1$-$C_6$-alkyl. $R^{13}$ and $R^{14}$ are preferably each independently selected from methyl, ethyl, 1-methylethyl, n-butyl, 1-methylpropyl, 2-methylpropyl, pentyl, 1-methylbutyl, 2-methylbutyl, 3-methylbutyl, hexyl, 1-methylpentyl, 2-methylpentyl, 3-methylpentyl, 4-methylpentyl, cyclopropyl, cyclobutyl, cyclopentyl or cyclohexyl.

Examples of preferred compounds of the formula (IX) are 1,3-bis(diphenylphosphinyl)-2-methylpropane, 1,3-bis(diphenylphosphinyl)-2,2-dimethylpropane, 1,3-bis(diphenylphosphinyl)-2-methyl-2-ethylpropane, 1,3-bis(diphenylphosphinyl)-2,2-diethylpropane, 1,3-bis(diphenylphosphinyl)-2-methyl-2-propylpropane, 1,3-bis(diphenylphosphinyl)-2-ethyl-2-propylpropane, 1,3-bis(diphenylphosphinyl)-2,2-dipropylpropane, 1,3-bis(diphenylphosphinyl)-2-methyl-2-butylpropane, 1,3-bis(diphenylphosphinyl)-2-ethyl-2-butylpropane, 1,3-bis(diphenylphosphinyl)-2-propyl-2-butylpropane, 1,3-bis(diphenylphosphinyl)-2,2-dibutylpropane, 1,3-bis(diphenylphosphinyl)-2-methyl-2-cyclopropylpropane, 1,3-bis(diphenylphosphinyl)-2-methyl-2-cyclobutylpropane, 1,3-bis(diphenylphosphinyl)-2-methyl-2-cyclopentylpropane, 1,3-bis(diphenylphosphinyl)-2-methyl-2-cyclohexylpropane, more preferably 1,3-bis(diphenylphosphinyl)-2,2-dimethylpropane and 1,3-bis(diphenylphosphinyl)-2-ethyl-2-butylpropane.

Preferred ligands of the catalytic system for the conversion in step (i) of the process according to the invention are the bidentate ligands of formula X

(X)

in which
V and W are independently selected from nitrogen, that optionally may be linked to a hydrogen atom, oxygen and sulfur, where nitrogen is incorporated as part of an amine, an imine or a nitrogen containing heterocycle, where oxygen is incorporated as an oxo substituent, as part of a hydroxy group, an alkoxy group or an oxygen containing heterocycle and where sulfur is incorporated as part of a thioketone group, a thiol group (—SH), an alkylthio group or a sulfur containing heterocycle;

T' is either absent or a methandiyl (—CH$_2$—) or a methendiyl (=CH—) bridge;

R$^{15}$ and R$^{16}$, independently from one another, are either absent or selected from hydrogen, C$_1$-C$_6$-alkyl, C$_2$-C$_6$-alkenyl or aryl, where the latter three radicals may optionally carry 1, 2 or 3 substituents selected from halogen, C$_1$-C$_4$-alkyl and C$_1$-C$_4$-haloalkyl; or if V and/or W are nitrogen, the respective radical R$^{15}$ and/or R$^{16}$ bonded thereto may be hydroxy or C$_1$-C$_4$-alkoxy;

R$^{17}$ and R$^{18}$ are independently selected from hydrogen, hydroxy, C$_1$-C$_6$-alkyl, C$_1$-C$_6$-alkoxy, C$_2$-C$_6$-alkenyl or aryl, where the latter four radicals may optionally carry 1, 2 or 3 substituents selected from halogen, C$_1$-C$_4$-alkyl and C$_1$-C$_4$-haloalkyl; or one or more pairs of moieties selected from T', R$^{15}$, R$^{16}$, R$^{17}$, and R$^{18}$ together with the atoms to which they are bound, form a 3-, 4-, 5-, 6- or 7-membered saturated, unsaturated or aromatic carbocyclic ring or a 3-, 4-, 5-, 6- or 7-membered saturated, unsaturated or aromatic heterocyclic ring containing 1, 2, or 3 heteroatoms selected from O, S and N as ring members, where the carbocyclic or heterocyclic ring may optionally carry 1, 2 or 3 substituents selected from halogen, C$_1$-C$_4$-alkyl and C$_1$-C$_4$-haloalkyl; and ---- is a single or double bond.

Preferred ligands of the formula X are selected from 1,2-diols, such as ethan-1,2-diol, 1,2-diamines, such as 1,2-diaminoethane, N,N'-dimethyl-1,2-diaminoethane, 1,2-diaminocyclohexane, e.g. trans-1,2-diaminocyclohexane, N,N'-dimethyl-1,2-diaminocyclohexane, e.g. trans-N,N'-dimethyl-1,2-diaminocyclohexane of formula XI (see below), 1,2-aminoalcohols, such as N-methyl-2-aminoethanol, 1,2- and 1,3-diketones, such as acetylacetone, hydroxylimines, such as the compounds of formulae XII and XIII below, cyclic carboxylic acids having usually 5, 6, 7 or 8 ring members, wherein the cycle contains besides carbon atoms one or two heteroatom(s) selected independently from S, O and N as ring members, and wherein a ring heteroatom is adjacent to the ring carbon atom that carries the carboxyl group such as L-proline and thiophene-2-carboxylic acid, polycyclic heteroaromatic compounds, such as 1,10-phenanthroline, heteroaromatic compounds, wherein two monocyclic heteroaromatic rings are linked via a single bond such as 2,2'-bipyridine, and diimines, such as N,N'-bis(2,6-diisopropylphenyl)ethandiimine, and wherein 2,2'-Bipyridine and 1,10-phenanthroline may be unsubstituted or substituted, in the case of the 1,10-phenanthroline preferably in the positions 4 and/or 7, with 1, 2, 3 or 4 substituents selected from C$_1$-C$_4$-alkyl, C$_3$-C$_7$-cycloalkyl, phenyl, phenoxy and phenylthio, where the phenyl ring in the last 3 radicals mentioned may carry 1, 2 or 3 substituents selected from halogen, C$_1$-C$_4$-haloalkyl and C$_1$-C$_4$-alkoxy.

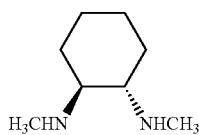

(XI)

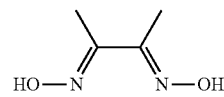

(XII)

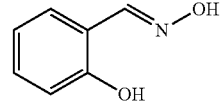

(XIII)

Furthermore, suitable catalytic systems for the conversion in step (i) of the process according to the invention are also those that comprise at least one N-heterocydlic carbene, known as NHC ligands. These are, more particularly, reactive complex ligands, which are described, for example, in G. A. Grasa et al., Organometallics 2002, 21, 2866. NHC ligands can be obtained in situ from imidazolium salts, for example 1,3bis(2,6-diisopropylphenyl)-4,5-H2-imidazolium chloride, with bases, and be converted to suitable catalysts in the presence of metal compounds such as palladium(0) compounds, especially those of the tris(dibenzylideneacetone)dipalladium(0) or bis-(dibenzylideneacetone)palladium(0) type, or palladium, copper and iron salts such as palladium(II) acetate, copper(II) triflate and iron(II) chloride. However, it is also possible to prepare NHC complex salts of metal compounds, e.g. (1,3-bis(2,6-diisopropylphenypimidazol-2-ylidene)(3-chloropyridyl)-palladium(II) dichloride, beforehand and to isolate them, and then to use them as preformed catalysts in the inventive cross-couplings (cf. S. P. Nolan, Org. Lett. 2005, 7, 1829 and M. G. Organ, Chem. Eur. J. 2006, 12, 4749).

For the inventive reactions, the NHC ligands used are preferably sterically hindered imidazol-2-ylidene compounds, especially those of the formula XIV which bear bulky R$^{19}$ and R$^{20}$ substituents in positions 1 and 3 of the imidazole ring. Preferably, R$^{19}$ and R$^{20}$ here are each independently aryl or hetaryl, each of which is unsubstituted or bears 1, 2, 3 or 4 substituents, where the substituents are preferably selected from C$_1$-C$_8$-alkyl and C$_3$-C$_7$-cycloalkyl. Particularly preferred R$^{19}$ and R$^{20}$ substituents are phenyl radicals which bear, in positions 2 and 6, preferably branched C$_1$-C$_6$-alkyl radicals.

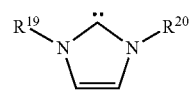

(XIV)

Said catalytic systems of the invention that comprise a NHC ligand, in particular those that are based on a palladium compound, may also bear at least one co-ligand. Such co-ligands are, for example, selected from hetaryl with at least one nitrogen atom in the ring, especially pyridyl which is unsubstituted or bears 1, 2 or 3 substituents selected from halogen, C$_1$-C$_6$-alkyl and C$_1$-C$_8$-alkoxy. A specific example of such a co-ligand is 3-chloropyridyl.

If the catalytic system comprises a palladium compound, then one or more ligands of the catalytic system for the conversion in step (i) are preferably selected from the monodentate phosphines of formula VII, the bidentate phosphines of formula VIII and the NHC ligands of formula XIV, and particularly preferably from those mentioned herein as preferred. In this context even more preferred ligands are methyl di-tert-butylphosphine, tri-tert-butylphosphine and X-Phos.

If the catalytic system comprises an iron compound, then one or more ligands of the catalytic system for the conversion in step (i) are typically selected from bidentate ligands, which are preferably ligands of formula X, in particular those mentioned herein as preferred. In this context preference is also given to ligands selected from 1,2-diamines, 1,3-diketones and cyclic carboxylic acids having usually 5, 6, 7 or 8 ring members, wherein the cycle contains besides carbon atoms one or two heteroatom(s) selected independently from S, O and N as ring members, and wherein a ring heteroatom is adjacent to the ring carbon atom that carries the carboxyl group, in particular those of these ligands that are of the formula X, such as specifically N,N'-dimethyl-1,2-diaminoethane, acetylacetone and L-proline.

If the catalytic system comprises a copper compound, then one or more ligands of the catalytic system for the conversion in step (i) are typically selected from bidentate ligands, which are preferably ligands of formula X, in particular those mentioned herein as preferred. In this context preference is also given to ligands selected from 1,2-diamines, hydroxylimines and cyclic carboxylic acids having usually 5, 6, 7 or 8 ring members, wherein the cycle contains besides carbon atoms one or two heteroatom(s) selected independently from S, 0 and N as ring members, and wherein a ring heteroatom is adjacent to the ring carbon atom that carries the carboxyl group, in particular those of these ligands that are of the formula X. More preference is given to 1,2-diamines of the formula X. Examples of suitable ligands in this regard are L-proline, thiophene-2-carboxylic acid and the compounds of the formulae XI, XII and XIII and in particular the compound of formula XI.

According to a preferred embodiment of the invention the catalytic system of the process of the invention comprises a copper compound and one or more, in particular one, ligand selected from ligands of formula X, in particular those that are mentioned herein as being preferably used in combination with a copper compound.

According to another preferred embodiment of the invention the one or more ligands, in particular one ligand, and the metal compound, in particular a copper compound, as precatalyst are charged separately to the reaction vessel and the catalytic system used in the process of the invention is formed thereafter. Preferably, the molar ratio of metal compound to ligand is in the range of 1:2 to 1:20, more preferably in the range of 1:5 to 1:15 and specifically 1:8 to 1:11. For example, it may be particularly advantageous to use 8 to 10 molar equivalents of complex ligand, based on one equivalent of the metal compound.

The metal compound of the catalytic system is used in the process according to the invention preferably in an amount of 0.1 to 15.0 mol %, preferably of 1.0 to 10.0 mol %, and especially of 3.0 to 7.0 mol %, based on the amount of the pyrazole derivative III used.

The reaction temperature of step (i) is determined by several factors, for example the reactivity of the reactants used and the type of the catalytic system selected, and can be determined by the person skilled in the art in the individual case, for example by simple preliminary tests. In general, the conversion in step (i) of the process according to the invention is performed at a temperature in the range from 0 to 250° C., preferably in the range from 20 to 200° C., more preferably in the range from 50 to 150° C. and specifically in the range from 70 to 120° C. Depending on the solvent used, the reaction temperature and on whether the reaction vessel possesses a vent, a pressure of generally 1 to 6 bar and preferably of 1 to 4 bar is established during the reaction.

The choice of base to be employed for the conversion in step (i) of the process of the invention depends on several factors, such as the reactivity of the reactants used and the type of the catalytic system selected, and can be determined by the person skilled in the art in the individual case, for example by simple preliminary tests. In general the base is selected from bases commonly known to be useful for similar reactions, such as tri-alkali metal phosphates, e.g. trisodium phosphate and tripotassium phosphate, alkali metal alkanolates, e.g. potassium isopropylate and sodium tert-butylate, and from alkali metal carbonates, e.g. sodium carbonate, potassium carbonate and rubidium carbonate. In this context preferred bases are tripotassium phosphate, sodium tert-butylate, rubidium carbonate and potassium carbonate.

In the process according to the invention the base is preferably used in an amount of 0.1 to 5 mol, more preferably of 0.1 to 3 mol, even more preferably of 0.2 to 2 mol and specifically of 0.3 to 1.7 mol, based in each case on 1 mol of the pyrazole derivative of the formula (III).

According to a preferred embodiment of the invention, in step (i), the phenyl halide of the formula II is used in an amount of 0.7 to 0.9 mol and the base is used in an amount of 0.2 to 2 mol, based in each case on 1 mol of the pyrazole derivative of the formula III, and, in addition, the complex ligand is used in an amount of 8 to 11 mol based on 1 mol of the metal compound.

According to a particular preferred embodiment of the invention, in step (i), the phenyl halide of the formula II is used in an amount of 0.75 to 0.85 mol and the base is used in an amount of 0.3 to 1.7 mol, based in each case on 1 mol of the pyrazole derivative of the formula III, and, in addition, the complex ligand is used in an amount of 8 to 10 mol based on 1 mol of the metal compound.

The present invention further provides a process for preparing a compound of the formula (IV),

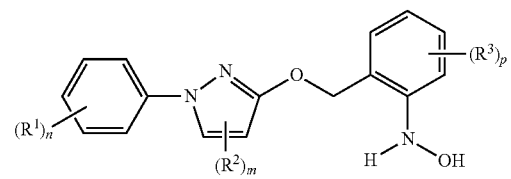

(IV)

in which
R$^1$, n, R$^2$, m, R$^3$ and p are each as defined herein before, comprising.
  (i) providing a 1-phenylpyrazole of formula (Ia) by reacting a phenyl halide of the formula (II) with a 3-benzyloxypyrazole IIIa, in which Y is nitro, according to the process described above,
and further,

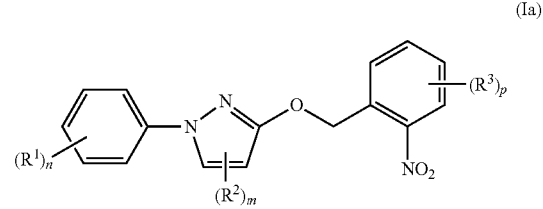

(Ia)

(ii) converting the 1-phenylpyrazole of the formula Ia to a N-phenylhydroxylamine IV.

Conversion into the 1-phenylpyrazole of the formula IV may be accomplished by hydrogenation which can be performed according to known methods for hydrogenating aromatic nitro compounds, e.g. by electrochemical reduction, by reduction with metals, such as zinc dust or amalgams, or, preferably, by catalytic hydrogenation as described for example in WO 96/22967 and WO 99/12911.

In case a catalytic hydrogenation process is used for the conversion in step (ii) of the inventive process the reaction is preferably performed in the presence of a commercial catalyst, such as platinum or palladium on a carrier, or Raney nickel or Raney cobalt. If a platinum or a palladium catalyst is to be used, it may have to be doped with sulfur or selenium in order to obtain sufficient selectivity, since the starting material, compound Ia, contains sensitive groups, such as a benzyl ether group and possibly halogens.

The conversion in step (ii) is preferably carried out by catalytic hydrogenation using a platinum or a palladium catalyst which in general contains platinum or palladium on a carrier material, such as carbon, graphite, barium sulphate or silicon carbide. The platinum or a palladium content of the catalyst is not critical and can be varied in wide limits.

A content of from 0.1 to 15% by weight, preferably from 0.5 to 10% by weight, based on the carrier material carbon is expedient. In relation to the compound Ia the amount of the platinum or palladium employed is in general from 0.001 to 1% by weight, preferably from 0.01 to 0.1% by weight.

Said catalytic hydrogenation using a platinum or a palladium catalyst is usually carried out in the presence of a base, which is preferably an amine, e.g. an aromatic amine such as pyridine, a heterocyclic amine such as piperidine or N-alkylmorpholine, or primary, secondary or tertiary aliphatic amines, such as triethylamine, diethylamine and n-propylamine. Preferably the hydrogenation is carried out in the presence of a primary $C_1$-$C_4$ alkylamine, such as n-propylamine, isopropylamine, n-butylamine or tert-butylamine, with n-propylamine being particularly preferred.

The aforementioned amines, in particular the N-alkylmorpholines, may also act as solvent of the hydrogenation reaction. Preference is given, however, to carrying out the hydrogenation in a mixture of an inert aprotic solvent with an amine, in particular an amine selected from those mentioned above as preferred. Suitable inert aprotic solvents are e.g. aliphatic or alicyclic ethers, such as THF or aliphatic or aromatic hydrocarbons, such as benzene, toluene or chlorobenzene. Preferred inert aprotic solvents are aromatic hydrocarbons, in particular toluene.

For said catalytic hydrogenation in step (ii) the amine is used, as a rule, in a concentration of from 1 to 20% by weight, preferably from 5 to 17% by weight, based on the solvent. Higher concentrations are possible but usually result in scarcely any improvements in the yield and selectivity and are therefore uneconomical. In relation to the compound Ia to be hydrated the amine is typically used in a molar ratio of from 1 to 15, preferably in a molar ratio of from 2 to 12.

The chosen temperature range for the catalytic hydrogenation is from −20° C. to +30° C., preferably from −5 to +10° C. The minimum temperature is determined only by the freezing point of the solvent used. The maximum temperature is dependent on the compound Ia to be hydrogenated and on the reaction parameters. To avoid overhydro-genation, a pressure which is from atmospheric pressure to 10 bar gauge pressure is established at the temperature at which the hydrogenation usually takes place sufficiently rapidly. In general, the hydrogen gas is introduced into the hydrogenation reactor at atmospheric or slightly superatmospheric pressure.

The starting materials need not be present in dissolved form for carrying out the novel process. The reaction usually gives optimum results even in suspension.

After the end of the reaction, a major part of the added amine is removed by distilling it off and/or by extraction with water. The distillation is preferably carried out under nitrogen or at reduced pressure. In the case of sensitive hydroxylamines IV complete absence of oxygen may be required.

Since the handling of the generally oxygen-sensitive hydroxylamines is difficult in some cases, it may be advantageous to process the hydroxylamines IV further immediately after removal of the aliphatic amine by extraction or distillation. In the removal of the amine by distillation, it is advantageous if the amine has a lower boiling point than the solvent. In this way a solution of the hydroxylamine in the solvent is obtained and can be further processed immediately, for instance in step (iii) of the process of the invention.

The present invention further provides a process for preparing a compound of the formula (V)

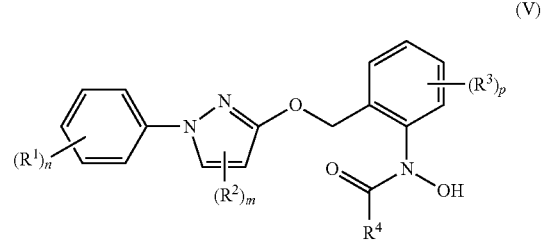

in which $R^1$, n, $R^2$, m, $R^3$, p and $R^4$ are each as defined herein before, comprising (i) providing a 1-phenylpyrazole of formula (Ia) by reacting a phenyl halide of the formula (II) with a 3-benzyloxypyrazole IIIa, in which Y is nitro, according to the process described above, followed by (ii) converting the 1-phenylpyrazole of the formula Ia to a N-hydroxylamine of the formula IV and, further (iii) converting the compound of the formula IV into a compound of the formula V.

Conversion into a compound of the formula V involves N-acylation of the compound of the formula IV. The N-acylation of compound IV in step (iii) can be performed according to known methods for acylating aromatic hydroxylamines, e.g. those described in WO 96/01256 and WO 99/12911.

The hydroxylamine of the formula IV produced in step (ii) is preferably without further purification directly introduced into step (iii) as crude product that is obtained after removal of the amine by distillation or extraction.

The N-acylation in step (iii) is generally carried out by reacting a hydroxylamine of the formula IV with a reagent of the formula (XV)

in which $R^4$ is as defined herein before and $L^1$ is a leaving group that is typically hydroxyl, halide, especially chloride or bromide, an —OR²¹ radical or an —O—CO—R²² radical, where the definitions of the R²¹ and R²² substituents are explained hereinafter.

When the reagent XV is used with L¹ being a hydroxyl group (R⁴—COOH), the reaction can be performed in the presence of a coupling reagent. Suitable coupling reagents (activators) are known to those skilled in the art and are selected, for example, from carbodiimides such as DCC (dicyclohexylcarbodiimide) and DCI (diisopropylcarbo-diimide), benzotriazole derivatives such as HBTU ((O-benzotriazol-1-yl)-N,N',N'-tetramethyluronium hexafluorophosphate) and HCTU (1H-benzotriazolium-1-[bis(dimethylamino)methylene]-5-chlorotetrafluoroborate), and phosphonium activators such as BOP ((benzotriazol-1-yloxy)tris(dimethylamino)phosphonium hexafluorophosphate), Py-BOP ((benzotriazol-1-yloxy)tripyrrolidinephosphonium hexafluorophosphate) and Py-BrOP (bromotripyrrolidinephosphonium hexafluorophosphate). In general, the activator is used in excess. The benzotriazole and phosphonium coupling reagents are generally used in a basic medium.

Suitable acylating reagents XV are also derivatives of compounds R⁴—COOH that can react with the hydroxylamine IV to give the hydroxylamide V, for example esters R⁴—C(O)—OR²¹ (L¹=OR²¹), acid halides R⁴—C(O)X in which X is a halogen atom (L¹=halogen), or acid anhydrides R⁴—C(O)—O—(O)C—R²² (L¹=—O—C(O)—R²²).

The acid anhydride R⁴—C(O)—O—(O)C—R²² is either a symmetric anhydride R⁴—C(O)—O—(O)C—R⁴ or an asymmetric anhydride, in which —O—(O)C—R²² is a group which can be displaced readily by the hydroxylamine IV used in the reaction. Suitable acid derivatives which can form suitable mixed anhydrides with the compound R⁴—COOH are, for example, the esters of chloroformic acid, e.g. isopropyl chloroformate and isobutyl chloroformate, or of chloroacetic acid.

Suitable esters R⁴—COOR²¹ derive preferably from alkanols R²¹—OH in which R²¹ is $C_1$-$C_4$-alkyl, such as methanol, ethanol, propanol, isopropanol, n-butanol, butan-2-ol, iso-butanol and tert-butanol, preference being given to the methyl and ethyl esters (R²¹=methyl or ethyl). Suitable esters may also derive from $C_2$-$C_6$-polyols, such as glycol, glycerol, trimethylolpropane, erythritol, pentaerythritol and sorbitol, preference being given to the glyceryl ester. When polyol esters are used, it is possible to use mixed esters, i.e. esters with different R²¹ radicals.

Alternatively, the ester R⁴—COOR²¹ is a so-called activated ester, which is obtained in a formal sense by the reaction of compound R⁴—COOH with an activated ester-forming alcohol, such as p-nitrophenol, N-hydroxybenzotriazole (HOBt), N-hydroxysuccinimide or OPfp (pentafluorophenol).

Alternatively, the reagent XV used for the N-acylation in step (iii) may possess another conventional leaving group L¹, for example pyrrolyl or imidazolyl.

The inventive N-acylations with the above-described reagents of the formula XV can be performed analogously to known processes.

Preference is given to using, for the N-acylation of compounds of the formula IV, carbonyl halides of the formula (XV), especially those in which the leaving group L¹ is chlorine or bromine, and in particular is chlorine. To this end, preferably 0.5 to 2 mol and especially 0.8 to 1.7 mol of the carbonyl chloride XV are used per 1 mol of the compound IV.

The acylation is advantageously carried out in the presence of an inert organic solvent which was used in the hydrogenation in previous step (ii), for example in an aprotic solvent, such as an aliphatic or aromatic hydrocarbon, e.g. toluene, xylene, heptane or cyclohexane, or in an aliphatic or cyclic ether, preferably DME, THF or dioxane. It is also possible to add a polar aprotic solvent, such as an aliphatic ketone, preferably acetone, an amide, preferably DMF, or a sulfoxide, preferably DMSO, ureas, e.g. tetramethylurea or 1,3-dimethyltetrahydro-2(1H)-pyrimidinone, a carboxylic ester, such as ethyl acetate, or a halogenated aliphatic or aromatic hydrocarbon, such as dichloromethane or chlorobenzene, to the reaction mixture.

As a rule, the reaction is carried out in the presence of an inorganic base, such as sodium hydroxide, potassium hydroxide, sodium carbonate, sodium bicarbonate, potassium carbonate or potassium bicarbonate, an amine, such as triethylamine, pyridine or N,N-diethylaniline, or an alkali metal alcoholate, e.g. sodium methylate or ethylate or potassium tert-butylate. However, the base is not absolutely essential and can be omitted or may, if required, be replaced by other acid acceptors, for example basic ion exchangers or water.

The reaction can also be carried out in a biphasic system consisting of an aqueous phase, that may or may not contain a base, such as alkali metal or alkaline earth metal hydroxides or carbonates, and a second phase that is based on at least one essentially water-immiscible organic solvent. Suitable phase-transfer catalysts that may be present in the reaction medium are, for example, ammonium halides and tetrafluoroborates and phosphonium halides.

The reaction temperature of the acylation is in general from −30° C. to the reflux temperature of the solvent used, preferably from −20 to 50° C.

The workup of the reaction mixtures obtained via the N-acylation reaction in step (iii) and the isolation of the compound of the formula (V) are effected in a customary manner, for example by filtering off the precipitated reaction product V, by an aqueous extractive workup, by removing the solvent, for example under reduced pressure, or by a combination of these measures. Further purification can be effected, for example, by crystallization, distillation or chromatography.

The present invention further provides a process for preparing a compound of the formula (VI)

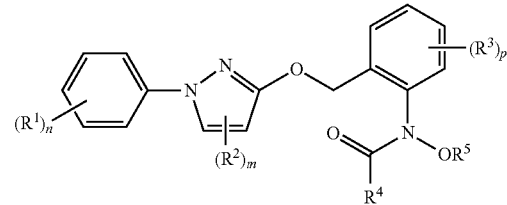

(VI)

in which
R¹, n, R², m, R³, p, R⁴ and R⁵ are each as defined herein before,
comprising
(i) providing a 1-phenylpyrazole of formula (Ia) by reacting a phenyl halide of the formula (II) with a 3-benzyloxy-pyrazole IIIa, in which Y is nitro, according to the process described above, followed by
(ii) converting the 1-phenylpyrazole of the formula Ia to a N-hydroxylamine of the formula IV,
(iii) converting the compound of the formula IV into a compound of the formula V and, further,
(iv) converting the compound of the formula V into a compound of the formula VI.

Conversion into a compound of the formula VI involves O-alkylation to the corresponding compound V. The O-alkylation of N-hydroxylamide V in step (iv) can be performed according to known methods for O-alkylating aromatic N-hydroxylamides, e.g. those described in WO 96/01256 and WO 99/12911.

The O-alkylation in step (iv) is generally carried out by reacting a compound V with a reagent of the formula (XVI)

$$R^5\text{-}L^2 \quad (XVI)$$

in which $R^5$ is as defined herein before and $L^2$ is a leaving group that is typically a halide, especially chloride or bromide, a sulfate, a sulfonate, preferably a methanesulfonate (mesylate), benzenesulfonate, o-toluenesulfonate (tosylate), p-bromobenzene-sulfonate (brosylate) or trifluoromethanesulfonate (triflate), or a diazo group.

Preferred reagents XVI are the halides and, in case $R^5$ is methyl, dimethyl sulfate.

The alkylation in step (iv) of the inventive process is usually carried out in an inert solvent or diluent, preferably in the presence of a base.

Examples of suitable solvents or diluents are those mentioned with respect to the N-acylation in step (iii) described above.

Suitable bases are inorganic bases, for example carbonates, such as potassium carbonate or sodium carbonate, bicarbonates, such as potassium bicarbonate or sodium bicarbonate, hydroxides, such as sodium hydroxide or potassium hydroxide, alkali metal hydrides, for example sodium hydride or potassium hydride, organic bases, such as amines, eg. triethylamine, pyridine or N,N-diethyl-aniline, and alkali metal alcoholates, such as sodium methylate or ethylate or potassium tert-butylate.

Preferably, the reagent XVI (for example dimethyl sulfate) and the N-acylated hydroxylamine V are initially taken and the base (for example potassium hydroxide) is metered in.

The amount of base or reagent XVI is preferably from half the molar amount to twice the molar amount, based on the amount of the compound V. Base and reagent XVI are particularly preferably used in a slight excess.

In general, the reaction temperature in the alkylation is from −78° C. to the boiling point of the reaction mixture, preferably from −30 to 100° C. and particularly preferably from 10 to 90° C.

As in the case of the N-acylation in step (iii), the O-alkylation, too, can be carried out in a biphasic system. The abovementioned phase-transfer catalysts may be used.

The workup of the reaction mixtures obtained via the O-alkylation reaction in step (iv) and the isolation of the compound of the formula VI are effected in a customary manner, for example by measures mentioned before regarding the N-acylation product V from step (iii).

The processes of the invention that include step (i) allow preparation, with a low level of complexity and in good yields and selectivities, of 1-phenylhalides I which are suitable starting compounds for preparing the N-hydroxylamines IV, N-hydroxylamides V and N-alkoxyamides VI obtainable therefrom according to processes of the invention including steps (ii), (iii) and (iv), respectively.

In a further aspect the invention relates to the 3-benzyloxypyrazoles of the formula (IIIa)

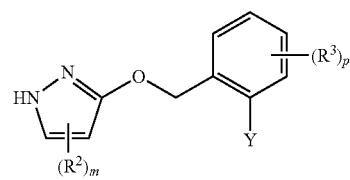

(IIIa)

in which
Y is nitro, a group $R^a$, a group $R^b$, a group $R^c$ or a group $R^d$,

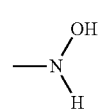

($R^a$)

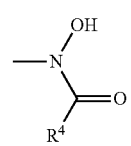

($R^b$)

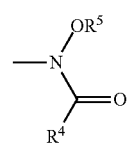

($R^c$)

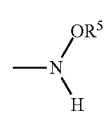

($R^d$)

each $R^2$ is independently selected from cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkoxycarbonyl;
   m is 0, 1 or 2;
   each $R^3$ is independently selected from halogen, cyano, $C_1$-$C_4$-haloalkyl, $C_1$-$C_4$-alkoxy and $C_1$-$C_4$-haloalkoxy, and
   p is 0, 1, 2 or 3.
Preference is given to compounds IIIa in which the variables Y, $R^2$, m, $R^3$ and p have the aforementioned preferred meanings.

The invention is further illustrated by the following non-limiting examples.

EXAMPLES

I. Preparation of the 3-benzyloxypyrazoles of the formula (IIIa)

I.3-Hydroxy-1H-pyrazole

Hydrazin hydrate (80% in $H_2O$, 6.7 mL, 110 mmol) was slowly added to a solution of (E)-methyl methoxyacrylate (11.6 g, 100 mmol) in 10 mL of methanol. The solution was heated to reflux for 90 min upon complete addition. Then, all volatiles were removed under reduced pressure to give the product as a slightly yellow solid (8.2 g, 97.5 mmol, 98% yield) that was sufficiently pure for further transformations.
   $^1$H NMR (DMSO-$d_6$, 500 MHz): δ (ppm)=10.40 (bs, 1H); 7.35 (d, J=3.0 Hz, 1H); 5.44 (d, J=3.0 Hz, 1H).

$^{13}$C NMR (DMSO-d$_6$, 125 MHz): δ (ppm)=161.0; 130.1; 89.3.

Melting point: 137° C.

I.2 1-Acetyl-3-hydroxy-1H-pyrazole

A solution of 3-hydroxy-1H-pyrazole (8.2 g, 97.5 mmol) in pyridine (40 mL) was heated to 95° C. A mixture consisting of acetic anhydride (9.4 mL, 102 mmol) and pyridine (20 mL) was added over 15 min; then stirring at 95° C. was continued for 60 min. All volatiles were then removed under reduced pressure and to the residue was added 200 mL of diethyl ether. The slurry was stirred overnight at room temperature, then the solid was filtered off and rinsed with diethyl ether. The product was obtained as an off-white solid (10.3 g, 81.7 mmol, 84% yield).

$^1$H NMR (DMSO-d$_6$, 500 MHz): δ (ppm)=10.95 (s, 1H); 8.13 (d, J=3.0 Hz, 1H); 6.00 (d, J=3.0 Hz, 1H), 2.48 (s, 3H).
$^{13}$C NMR (DMSO-d$_6$, 125 MHz): δ (ppm)=167.9; 163.9; 129.8; 99.8; 21.3.

Melting point: 191° C.

I.3 3-(2-Nitrobenzyloxy)-1H-pyrazole

A suspension of 1-acetyl-3-hydroxy-pyrazole (3.4 g, 27.0 mmol), 2-nitrobenzyl bromide (5.9 g, 27.3 mmol) and K$_2$CO$_3$ (4.0 g, 28.9 mmol) in 75 mL of 2-butanone was heated to reflux for 90 min. After cooling to room temperature, the precipitated salts were filtered off and rinsed with tert-butyl methyl ether (TBME). The filtrate was then concentrated under reduced pressure (50 mbar) and redissolved in a mixture of tetrahydrofuran (THF) and methanol (MeOH) (3:2, 50 mL). 2 mL of a 10% NaOH solution were added and the solution was stirred 60 min at ambient temperature. Then, all volatiles were removed under reduced pressure (50 mL). The residue was diluted with 20 mL of H$_2$O and 30 mL of ethyl acetate (EtOAc). The aqueous phase was extracted with EtOAc (2×20 mL). The combined org. layers were washed with water and brine (both 30 mL) and dried over Na$_2$SO$_4$. The crude product was obtained after evaporation of all volatiles and recrystallised from dichloromethane (15 mL) to give the product as yellowish crystals (5.0 g, 22.8 mmol, 84%).

$^1$H NMR (DMSO-d$_6$, 500 MHz): δ (ppm)=11.93 (s, 1H); 8.10 (d, J=8.0 Hz, 1H); 7.77-7.80 (m, 2H); 7.58-7.62 (m, 1H); 7.54 (d, J=2.5 Hz, 1H); 5.74 (d, J=2.5 Hz, 1H); 5.59 (s, 2H).
$^{13}$C NMR (DMSO-d$_6$, 125 MHz): δ (ppm)=162.3; 147.3; 133.8; 133.1; 130.1; 129.0; 128.8; 124.5; 89.4; 66.6.

Melting point: 87° C.

I.4 3-(2-Bromobenzyloxy)-1H-pyrazole

A suspension of 1-acetyl-3-hydroxy-pyrazole (1.0 g, 7.9 mmol), 2-bromobenzyl bromide (2.0 g, 7.9 mmol) and K$_2$CO$_3$ (1.2 g, 8.4 mmol) in 20 mL of 2-butanone was heated to reflux for 90 min. After cooling to room temperature, the precipitated salts were filtered off and rinsed with tert-butyl methyl ether (TBME). The filtrate was then concentrated under reduced pressure (50 mbar) and redissolved in a mixture of tetrahydrofuran (THF) and methanol (MeOH) (3:2, 25 mL). 1 mL of a 10% NaOH solution was added and the solution was stirred 60 min at ambient temperature. Then, all volatiles were removed under reduced pressure (50 mL). The residue was diluted with 10 mL of H$_2$O and 20 mL of ethyl acetate (EtOAc). The aqueous phase was extracted with EtOAc (2×10 mL). The combined organic layers were washed with water and brine (both 20 mL) and dried over Na$_2$SO$_4$. The crude product was obtained after evaporation of all volatiles and used in the next step without further purification (1.9 g, 7.5 mmol, 95%).

$^1$H NMR (CDCl$_3$, 500 MHz): δ (ppm)=7.56 (d, J=8.0 Hz, 2H); 7.36 (d, J=1.5 Hz, 1H); 7.30 (t, J=7.5 Hz, 1H); 7.17 (dt, J=1.5 Hz, J=8.0 Hz, 1H); 5.80 (d, J=2.5 Hz, 1H); 5.30 (s, 2H).
$^{13}$C NMR (CDCl$_3$, 125 MHz): δ (ppm)=163.4; 136.5; 132.6; 130.3; 129.2; 129.1; 127.5; 122.5; 90.8; 70.4.

I.5 Methyl N-{2-[3'-(1H-pyrazol)-yloxymethyl]-phenyl}-N-methoxycarbamate

A suspension of 1-acetyl-3-hydroxy-pyrazole (0.6 g, 5.1 mmol), methyl N-(2-bromomethylphenyl)-N-methoxycarbamate (~70% purity, 2.0 g, 5.1 mmol) and K$_2$CO$_3$ (0.9 g, 6.6 mmol) in 20 mL of 2-butanone was heated to reflux for 90 min. The mixture was then cooled to room temperature and filtered. The filtrate was concentrated and subjected to column chromatography (SiO$_2$, hexane/ethyl acetate =100:0 to 80:20) to give the product as a tan liquid (0.9 g, 3.3 mmol, 65% yield). The acetylated compound (0.73 g, 2.3 mmol) was dissolved in 7 mL of methanol. 60 μL of triethyl amine were added and the solution was stirred for 60 min at room temperature. Then, all volatiles were removed under reduced pressure and the residue was subjected to flash column chromatography (SiO$_2$, hexane/ethyl acetate=100:0 to 80:20) to give the product as an off-white solid (0.53 g, 1.9 mmol, 83% yield).

II. Preparation of 1-phenylpyrazoles of the formula (I)

II.1 1-(4-Chlorophenyl)-3-(2-nitrobenzyloxy)pyrrazole

II.1a Conversion with 4-chlorophenyl bromide

A suspension consisting of 3-(2-nitrobenzyloxy)-1H-pyrazole (0.20 g, 0.91 mmol), 4-chlorobromobenzene (0.14 g, 0.73 mmol), CuI (9 mg, 0.05 mmol), K$_2$CO$_3$ (0.19 g, 1.4 mmol) and N,N'-dimethylcyclohexanediamine (72 μL, 0.46 mmol) in 2.0 mL of toluene was heated to 100° C. for 20 h. The mixture was then cooled to rt and directly subjected to column chromatography (SiO2, hexane/ethyl acetate=100:0 to 80:20). The product was obtained as a yellow solid (180 mg, 0.55 mmol, 75%).

$^1$H NMR (DMSO-d$_6$, 500 MHz): δ (ppm)=8.39 (d, J=3.0 Hz, 1H); 8.13 (dd, J=1.0 Hz, J=8.0 Hz, 1H); 7.84 (dd, J=1.5 Hz, J=8.0 Hz, 1H); 7.80 (dt, J=1.5 Hz, J=7.0 Hz, 1H); 7.75 (td, J=2.5 Hz, J=9.0 Hz, 2H); 7.63 (dt, J=2.0 Hz, J=7.8 Hz, 1H); 7.50 (dd, J=2.5 Hz, J=9.0 Hz, 2H); 6.15 (d, J=2.5 Hz, 1H); 5.65 (s, 2H).
$^{13}$C NMR (DMSO-d$_6$, 125 MHz): δ (ppm)=163.4; 147.5; 138.3; 133.9; 132.3; 129.7; 129.4; 129.3; 129.2; 129.1; 124.7; 118.6; 94.5; 66.9.

Melting point: 140° C.

II.1b Conversion with 4-chloroiodobenzene

Following the procedure analogously to that described in 11.1a, but using 4-chloroiodobenzene gave a yield of 54% together with 2% of the undesired regioisomer.

II.2 1-(4-Chlorophenyl)-3-(2-bromobenzyloxy-)-1H-pyrazole

A suspension consisting of 3-(2-bromobenzyloxy)-1H-pyrazole (0.20 g, 0.91 mmol), 4-chloroiodobenzene (0.17 g, 0.73 mmol), CuI (9 mg, 0.05 mmol), K₂CO₃ (0.05 mg, 0.38 mmol) and N,N'-dimethylcyclohexanediamine (72 μL, 0.46 mmol) in 2 mL of toluene was heated to 100° C. for 20 h. The mixture was then cooled to room temperature and directly subjected to column chromatography (SiO₂, hexane/ethyl acetate=100:0 to 80:20). The product was obtained as a colorless solid (140 mg, 0.14 mmol, 53% yield).

$^1$H NMR (CDCl₃, 500 MHz): δ (ppm)=7.71 (d, J=3.0 Hz, 1H); 7.58-7.61 (m, 2H); 7.56 (d, J=9.0 Hz, 2H); 7.37 (d, J=9.0 Hz, 2H); 7.34 (t, J=8.0 Hz, 1H); 7.19 (dt, J=1.5 Hz, J=7.5 Hz, 1H); 5.97 (d, J=2.5 Hz, 1H); 5.39 (s, 2H).

$^{13}$C NMR (CDCl₃, 125 MHz): δ (ppm)=164.2; 136.4; 13.7; 130.7; 129.5; 129.4; 129.3; 127.8; 127.5; 122.9; 119.0; 94.5; 70.3.

Melting point: 45° C.

II.3 Methyl N-{2-[3'-(1-(4-chloro-phenyl)-1H-pyrazol)-yloxymethyl]-phenyl}-N-methoxycarbamate A suspension consisting of methyl N-{2-[3'-(1H-pyrazol)-yloxymethyl]-phenyl}-N-methoxycarbamate (0.25 g, 0.91 mmol), 4-chlorobromobenzene (0.14 g, 0.73 mmol), CuI (9 mg, 0.05 mmol), K₂CO₃ (0.05 mg, 0.38 mmol) and N,N'-dimethylcyclohexanediamine (72 μL, 0.46 mmol) in 2 mL of toluene was heated to 100° C. for 20 h. The mixture was then cooled to room temperature and directly subjected to column chromatography (SiO₂, hexane/ethyl acetate=100:0 to 80:20). The product was obtained as an off-white oil (91 mg, 0.23 mmol, 32% yield).

$^1$H NMR (DMSO-d₆, 500 MHz): δ (ppm)=7.61-7.62 (m, 1H); 7.60 (d, J=2.5 Hz, 1H); 7.44 (d, J=9.0 Hz, 2H); 7.30-7.36 (m, 2H); 7.26 (d, J=9.0 Hz, 2H); 7.20 (t, J=7.5 Hz, 1H); 5.87 (d, J=2.5 Hz, 1H); 5.36 (s, 2H); 3.73 (s, 3H); 3.72 (s, 3H).

$^{13}$C NMR (DMSO-d₆, 125 MHz): δ (ppm)=164.2; 155.8; 138.6; 137.5; 134.8; 130.4; 129.2; 128.9; 128.8; 128.5; 127.8; 127.1; 118.8; 94.5; 66.9; 62.0; 53.4.

The invention claimed is:

1. A compound of the formula (IIIa)

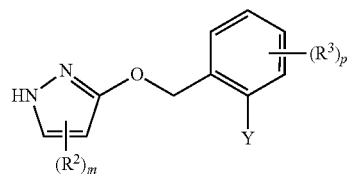

in which
each $R^2$ is independently selected from cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkoxycarbonyl;
each $R^3$ is independently selected from halogen, cyano, $C_1$-$C_4$-alkyl, $C_1$-$C_4$-haloalkyl, $C_1$-$C_4$-alkoxy and $C_1$-$C_4$-haloalkoxy, m is 0, 1 or 2;
p is 0, 1, 2 or 3,
Y is nitro, a group $R^a$, a group $R^b$, a group $R^c$ or a group $R^d$,

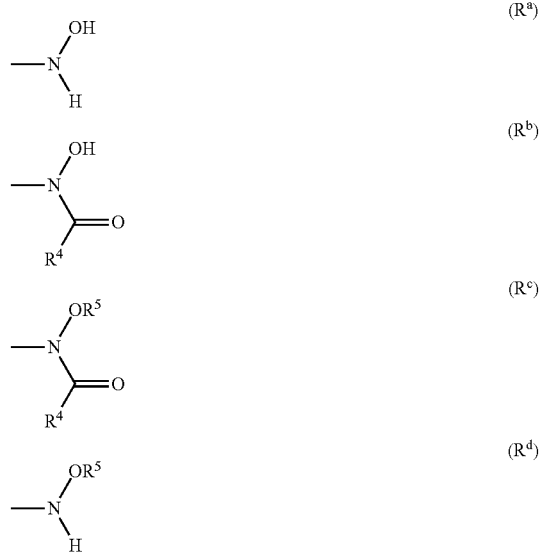

in which
$R^4$ is H, $C_1$-$C_4$-alkyl, $C_1$-$C_4$-haloalkyl, $C_1$-$C_4$-alkoxy, $C_1$-$C_4$-haloalkoxy, aryl, aryloxy, aryl-$C_1$-$C_4$-alkoxy, where the aryl groups in the three latter radicals optionally bear 1, 2, 3 or 4 substituents which are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and
$R^5$ is $C_1$-$C_4$-alkyl, $C_1$-$C_4$-haloalkyl or aryl-$C_1$-$C_4$-alkyl, where the aryl group in the latter radical optionally bears 1, 2, 3 or 4 substituents which are selected from halogen, cyano, nitro, $C_1$-$C_4$-alkyl, $C_1$-$C_4$-haloalkyl, $C_1$-$C_4$-alkoxy and $C_1$-$C_4$-haloalkoxy.

2. The compound of claim 1, wherein m is 0.
3. The compound of claim 1, wherein p is 0 or 1.
4. The compound of claim 1, wherein p is 1 and $R^3$ is located meta or para to the attachment point of the methylene bridge.
5. The compound of claim 1, wherein $R^3$ is chlorine, fluorine, $C_1$-$C_2$-alkyl or $C_1$-$C_2$-haloalkyl.
6. The compound of claim 1, wherein $R^4$ is methoxy, halomethoxy or benzyloxy.
7. The compound of claim 1, wherein $R^5$ is methyl or halomethyl.
8. The compound of claim 1, wherein Y is nitro or a group $R^c$.
9. The compound of claim 1, wherein Y is nitro or a group $R^c$ and wherein m is 0 and p is 0.

* * * * *